US012465300B1

(12) United States Patent
Bauernfeind et al.

(10) Patent No.: US 12,465,300 B1
(45) Date of Patent: Nov. 11, 2025

(54) DETENT-FREE LOCKING OF AN ADDITIONAL BODY RELATIVE TO A BASE BODY

(71) Applicant: Siemens Healthineers AG, Forchheim (DE)

(72) Inventors: Michael Bauernfeind, Schwarzenbach (DE); Moritz Weber, Nuremberg (DE); Joern Wutz, Kemnath (DE); Michael Schweiger, Bayreuth (DE)

(73) Assignee: SIEMENS HEALTHINEERS AG, Forchheim (DE)

( * ) Notice: Subject to any disclaimer, the term of this patent is extended or adjusted under 35 U.S.C. 154(b) by 0 days.

(21) Appl. No.: 19/199,552

(22) Filed: May 6, 2025

(30) Foreign Application Priority Data

May 7, 2024 (DE) ..................... 10 2024 204 264.1

(51) Int. Cl.
*A61B 6/04* (2006.01)
*A61G 7/005* (2006.01)
*A61G 13/04* (2006.01)

(52) U.S. Cl.
CPC ............ *A61B 6/0407* (2013.01); *A61G 7/005* (2013.01); *A61G 13/04* (2013.01)

(58) Field of Classification Search
CPC ......... A61B 6/0407; A61B 6/04; A61B 6/105; A61G 7/005; A61G 13/04
See application file for complete search history.

(56) References Cited

U.S. PATENT DOCUMENTS

| | | | | |
|---|---|---|---|---|
| 53,706 A * | 4/1866 | Tucker | A47C 23/04 | 5/1 |
| 4,452,439 A * | 6/1984 | Hogan | A61B 6/04 | 5/601 |
| 6,470,519 B1 * | 10/2002 | Pattee | A61G 13/02 | 5/943 |
| 10,716,521 B2 * | 7/2020 | Van De Rijdt | A61B 6/0487 | |
| 2004/0172757 A1 * | 9/2004 | Somasundaram | A61G 13/02 | 5/601 |
| 2021/0315530 A1 * | 10/2021 | DeLong Samalik | A61B 8/40 | |

FOREIGN PATENT DOCUMENTS

| | | | | |
|---|---|---|---|---|
| CN | 109199727 A * | 1/2019 | A61G 7/05 |
| CN | 113827918 A * | 12/2021 | A63B 22/04 |
| CN | 113876509 A * | 1/2022 | A61G 7/0503 |
| CN | 114732427 A * | 7/2022 | A61B 6/0407 |
| DE | 202021101803 U1 | 6/2021 | |
| DE | 202021106772 U1 | 1/2022 | |
| GB | 2566160 A * | 3/2019 | A61G 13/06 |
| NO | 136907 B * | 8/1977 | A61G 7/005 |

OTHER PUBLICATIONS

German Office Action and English translation thereof for German Application No. 10 2024 204 264.1 mailed Feb. 4, 2025.

* cited by examiner

*Primary Examiner* — Eric J Kurilla
(74) *Attorney, Agent, or Firm* — Harness, Dickey & Pierce, P.L.C.

(57) ABSTRACT

An additional body of an apparatus is mounted on a base body of the apparatus and is movable along a path. Arranged on the base body is a locking structure. Arranged on the additional body is a toothed element. The locking structure and toothed element interact to block movement of the additional body.

20 Claims, 3 Drawing Sheets

DETENT-FREE LOCKING OF AN ADDITIONAL BODY RELATIVE TO A BASE BODY

CROSS-REFERENCE TO RELATED APPLICATION(S)

The present application claims priority under 35 U.S.C. § 119 to German Patent Application No. 10 2024 204 264.1, filed May 7, 2024, the entire contents of which are incorporated herein by reference.

FIELD

One or more example embodiments of the present invention are based on an apparatus,

- wherein the apparatus has a base body and an additional body,
- wherein the additional body is mounted on the base body via a guide, so that the additional body can move relative to the base body along a path determined by the guide,
- wherein a locking structure is arranged on the base body and a toothed element is arranged on the additional body, by the interaction of which a movement of the additional body relative to the base body can be blocked,
- wherein the toothed element has a plurality of first teeth, which when the additional body moves relative to the base body successively pass through an effective area of the locking structure, so that when the first teeth pass through the effective area of the locking structure a local direction of movement of the toothed element is defined which is valid for the effective area of the locking structure,
- wherein the first teeth, viewed in the local direction of movement, follow one another in a grid dimension,
- wherein the locking structure has a first locking element which comprises a number of second teeth and can move in a direction of actuation running orthogonally to the local direction of movement of the toothed element between a release position and an actuation position, but which is fixed in the local direction of movement of the toothed element,
- wherein in the release position the second teeth of the first locking element do not enter between the first teeth and consequently do not block the movement of the additional body relative to the base body,
- wherein in the actuation position the second teeth of the first locking element enter fully between the first teeth and consequently block the movement of the additional body relative to the base body.

BACKGROUND

In the case of patient couches, for example angiography tables, it is normally possible to move the table in the longitudinal direction. Furthermore, it is often possible to tilt the table about a horizontal transverse axis, so that, viewed in the longitudinal direction of the table, one end is arranged higher than the other end. Before tipping, the table must be locked in the longitudinal direction, since otherwise the table would shift by itself due to gravity. There must hence be a locking device present, by which the table, viewed in the longitudinal direction of the table, is held in its previously set position.

In the prior art a brake apparatus which has a brake disk and brake shoes is normally used to hold the table. The brake disk is arranged on the table and rotates when the table moves in the longitudinal direction. The brake shoes are arranged on a table base and can be actuated via an actuator-generally an electromagnetic actuator. This brake apparatus has the advantage that it can be actuated in any travel position. However, it requires a large installation space and is expensive. In addition, the brake disk increases the moment of inertia which has to be moved by an operator at the same time when the table is moved manually.

Furthermore, detent apparatuses are known in which a spring-loaded detent engages with a correspondingly designed toothed wheel or the like. Such detent apparatuses are simple, robust and inexpensive. However, locking is only possible at intervals defined by the grid dimension which the teeth of the toothed wheel or the like have. Such a detent apparatus is unsuitable for implementing locking in any travel position.

SUMMARY

An object of one or more example embodiments of the present invention is to create opportunities, by which an additional body which can be moved relative to a base body can be locked and held in any travel positions in a simple and reliable manner.

At least this object is achieved by an apparatus having the features as recited in the independent claim. Advantageous embodiments of the apparatus are the subject matter of the dependent claims.

In accordance with embodiments of the present invention, an apparatus of the type mentioned in the introduction is embodied in that the locking structure has, in addition to the first locking element, a second locking element which likewise comprises a number of second teeth and can move in a direction of actuation of the toothed element running orthogonally to the local direction of movement between a release position and an actuation position, but which is fixed in the local direction of movement of the toothed element. Furthermore, in the release position the second teeth of the second locking element do not enter between the first teeth and consequently do not block the movement of the additional body relative to the base body. Conversely, in the actuation position the second teeth of the second locking element enter fully between the first teeth and consequently block the movement of the additional body relative to the base body. In this respect, there is a correspondence between the first and the second locking element. However, an important difference is the coordination of the arrangement of the second teeth of both the locking elements relative to one another. This is because, viewed in the local direction of movement of the toothed element, the second teeth of the second locking element are offset by an odd-numbered multiple of half of the grid dimension compared to the second teeth of the first locking element. The offset is therefore half the grid dimension, one and a half times the grid dimension, two and a half times the grid dimension, etc.

The additional second locking element and the arrangement of its second teeth mean that whenever the arrangement of the second teeth of the first locking element corresponds exactly to the arrangement of the first teeth, the second teeth of the second locking element can enter fully between the first teeth. Conversely, if the arrangement of the second teeth of the second locking element corresponds exactly to the arrangement of the first teeth, the second teeth of the first locking element can enter fully between the first teeth. In these two extreme positions, a single one of both the locking elements fully blocks the movement of the additional body relative to the base body. In positions between both these positions, both locking elements can each partially enter between the first teeth with their second teeth, wherein the second teeth of both the locking elements rest on opposing flanks of the first teeth. Consequently, the one locking element prevents a forward movement of the additional body along the path, and the other locking element prevents a backward movement of the additional body along the path. As a result, the interaction of both the locking elements also results in a blocking of the movement of the additional body in positions between both these positions.

It is possible for the first and second locking element to each have only a single second tooth. However, it is generally preferable if the first and second locking element each have multiple second teeth. In this case, the second teeth of the respective locking element follow one another, viewed in the local direction of movement, in an integer multiple of the grid dimension, in particular in the grid dimension.

The respective locking element preferably rests on a respective stop in the respective release position in the respective direction of actuation. This makes it easy to create a defined respective release position.

In principle, both the locking elements can be operated via their own actuation elements. In this case, the directions of actuation of both the locking elements can also be selected independently of one another. However, it is considerably easier if the direction of actuation of the second locking element corresponds to the direction of actuation of the first locking element and the locking elements can be moved between their release positions and their actuation positions via a uniform actuation element.

The actuation element preferably acts on a connecting element, via which both the locking elements are connected to one another. This makes it particularly easy to act on both the locking elements.

In one region of the connecting element, the actuator preferably acts on the connecting element which is located between both the locking elements. In particular, this ensures an even exertion of force on both the locking elements.

The connecting element is preferably connected to at least one of the locking elements via an elongated hole. This reliably prevents both the locking elements from jamming against one another. Otherwise, such jamming of both the locking elements against one another could occur in particular if both the locking elements are not transferred evenly from the release position to the actuation position or vice versa.

A spring facility is preferably associated with the actuation element, and exerts a spring force on the actuation element, so that in the absence of other forces in the direction of actuation of the locking elements, the actuation element applies to the locking elements a force directed to the actuation position. This means in particular that it is possible to achieve a situation in which a release of the movement of the additional body relative to the base body must be carried out actively, whereas in the absence of such a release the movement is automatically blocked. The operational safety of the apparatus is consequently increased.

The actuation element is preferably designed as a toggle lever with a first and a second lever arm. This embodiment is simple, robust and reliable.

When the locking elements move from their release positions to their actuation positions, the actuation element preferably always passes through an intermediate position in which the first and the second lever arm form an angle of 180°, regardless of the extent by which the additional body has moved relative to the base body. This means that the toggle lever has a self-locking effect.

The path determined by the guide can be a circular path. Generally, however, the path determined by the guide is a linear path. Such a situation exists for example if the additional body is designed as a reclining table of a patient couch and the base body is designed as a support element of the patient couch which supports the reclining table.

BRIEF DESCRIPTION OF THE DRAWINGS

The above-described properties, features and advantages of the present invention and the manner in which they are achieved will become clearer and more readily comprehensible in connection with the following description of the exemplary embodiments, which are explained in greater detail in connection with the drawings, which schematically show.

DETAILED DESCRIPTION

Figure 1:
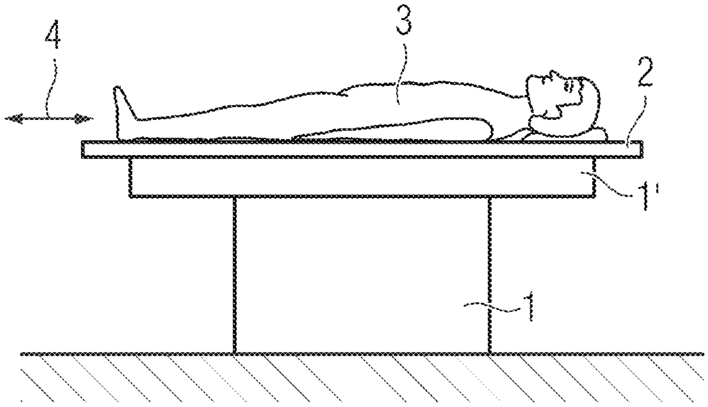
FIG. 1 an apparatus having a base body and an additional body.

In accordance with FIG. 1 an apparatus has a base body 1 and an additional body 2. The additional body 2 is mounted on the base body 1 via a guide. Consequently, the additional body 2 can move relative to the base body 1 along a path determined by the guide. In the present case the additional body 2 is designed as a reclining table of a patient couch. A patient 3 can thus be positioned on the patient couch. Furthermore, in the present case the base body 1 is designed as a support element of the patient couch which supports the reclining table. In principle, however, the apparatus can be of any nature. Furthermore, in accordance with FIG. 1 the path determined by the guide is a linear path. A double arrow 4 in FIG. 1 indicates the directions forward and backward in which the reclining table or generally the additional body 2 can be moved in the present case. Alternatively, it could however also be a circular path.

Figure 2:
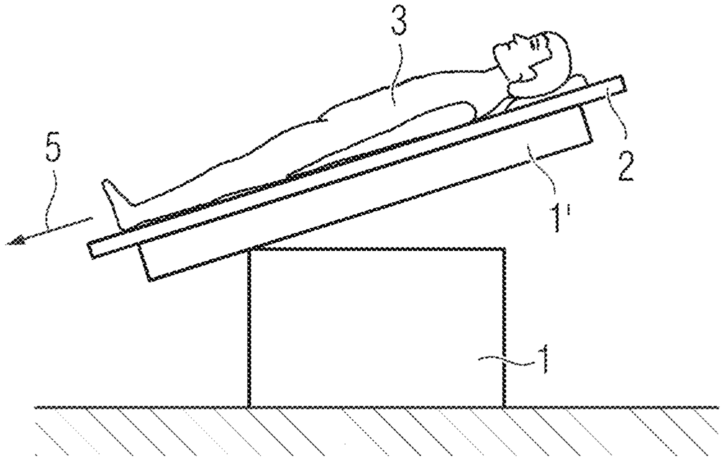
FIG. 2 a modification of the apparatus from FIG. 1.

In accordance with FIG. 2, for example in the case of a patient couch, an intermediate element 1', which can be regarded as part of the base body 1, can be raised on one side. Consequently, the reclining table is also raised on one side. If the reclining table could not be locked, the reclining table (where appropriate including the patient 3 situated on the reclining table) would move by itself into the lowest possible position due to gravity. This is indicated in FIG. 2 by an arrow 5 directed obliquely downward.

Figure 3:
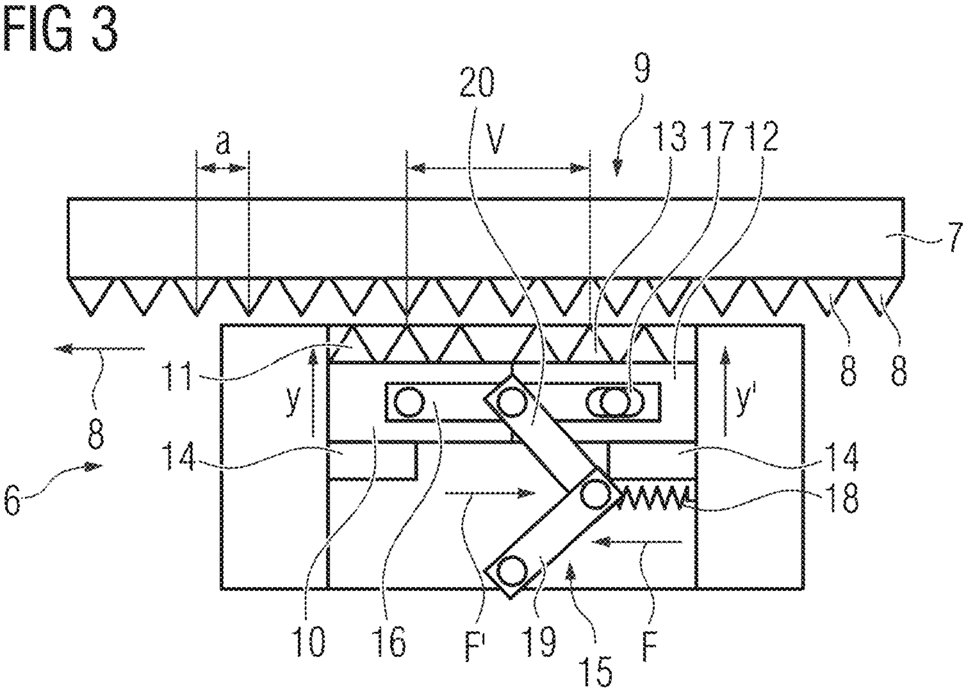
FIG. 3 a locking structure and a toothed element in a release position.

To prevent such an undesired travel movement of the reclining table or generally of the additional body 2 relative to the base body 1, in accordance with FIG. 3 a locking structure 6 is arranged on the base body 1 and furthermore a toothed element 7 is arranged on the additional body 2. The locking structure 6 and the toothed element 7 can interact, such that they block a movement of the additional body 2 relative to the base body 1. The toothed element 7 is in the present case a toothed rack, because the path is linear. If the path were circular, the toothed element 7 would be a toothed wheel.

The toothed element 7 has a plurality of teeth 8. Only a few of the teeth 8 in FIG. 3 (and also in FIGS. 4 to 6) are provided with their reference character. The teeth 8 are arranged such that when the additional body 2 moves relative to the base body 1, they pass consecutively through an effective area 9 of the locking structure 6. When the teeth 8 pass through the effective area 9 of the locking structure 6 a direction of movement x of the toothed element 7 is thus defined. It is possible for the direction of movement x to be uniform for the entire toothed element 7. However, the direction of movement x is valid at least locally for the effective area 9 of the locking structure 6. The teeth 8 follow one another, viewed in the local direction of movement x, in a grid dimension a. The teeth 8 of the toothed element 7 are referred to below as first teeth to distinguish them from teeth of other elements.

In accordance with FIG. 3 the locking structure 6 has a first locking element 10. The first locking element 10 comprises a number of teeth 11, referred to below as second teeth to distinguish them from the first teeth 8. Only one of the second teeth 11 in FIG. 3 (and also in FIGS. 4 to 6) is provided with its reference character. The number of second teeth 11 is generally greater than 1. The first locking element 10 thus generally has multiple second teeth 11. The second teeth 11 in this case follow one another, viewed in the local direction of movement x, in an integer multiple of the grid dimension a. In individual cases, it can be double, triple, etc. the grid dimension a. However, the second teeth 11 generally follow one another in the grid dimension a.

The first locking element 10 can move in a direction of actuation y. The direction of actuation y runs orthogonally to the local direction of movement x of the toothed element 7. However, the first locking element 10 is fixed in the local direction of movement x of the toothed element 7. In the local direction of movement x the first locking element 10 cannot therefore be moved.

The first locking element 10 can move in the direction of actuation y between a release position and an actuation position. If the first locking element 10 is in the release position (the first locking element 10 is shown in this position in FIG. 3), the second teeth 11 of the first locking element 10 do not enter between the first teeth 8 of the toothed element 7. Consequently, in the release position they do not block the movement of the additional body 2 relative to the base body 1. Conversely, if the first locking element 10 is in the actuation position (the first locking element 10 is shown in this position in FIG. 4), the second teeth 11 of the first locking element 10 enter fully between the first teeth 8. Consequently, in the actuation position they block the movement of the additional body 2 relative to the base body 1.

In accordance with FIG. 3 the locking structure 6 furthermore has a second locking element 12. The second locking element 12 likewise comprises a number of teeth 13, referred to below as second teeth 13 of the second locking element 12 to distinguish them from the first teeth 8 and the second teeth 11 of the first locking element 10. Only one of the second teeth 13 in FIG. 3 (and also in FIGS. 4 to 6) is provided with its reference character. The number of second teeth 13 of the second locking element 12 is generally greater than 1. The second locking element 12 thus generally has multiple second teeth 13. In this case the second teeth 13 of the second locking element 12 follow one another, viewed in the local direction of movement x, in an integer multiple of the grid dimension a. In individual cases, it can be double, triple, etc. the grid dimension a. However, the second teeth 13 of the second locking element 12 generally follow one another in the grid dimension a.

The second locking element 12 can move in a direction of actuation y'. The direction of actuation y' too runs orthogonally to the local direction of movement x of the toothed element 7. The direction of actuation y' of the second locking element 12 can in particular correspond to the direction of actuation y of the first locking element 10. However, the first locking element 10 is fixed in the local direction of movement x of the toothed element 7. It cannot therefore be moved in the local direction of movement x.

The second locking element 12 too can move in the direction of actuation y' between a release position and an actuation position. If the second locking element 12 is in the release position (the second locking element 12 is shown in this position in FIG. 3), the second teeth 13 of the second locking element 12 do not enter between the first teeth 8. Consequently, in the release position they do not block the movement of the additional body 2 relative to the base body 1. Conversely, if the second locking element 12 is in the actuation position (the second locking element 12 is shown in this position in FIG. 5), the second teeth 13 of the second locking element 12 enter fully between the first teeth 8. Consequently, in the actuation position they block the movement of the additional body 2 relative to the base body 1.

The structure, function and mode of operation of the second locking element 12 thus correspond to the structure, function and mode of operation of the first locking element 10. However, viewed in the local direction of movement x of the toothed element 7, the second teeth 13 of the second locking element 12 are offset by an odd-numbered multiple of half of the grid dimension a compared to the second teeth 11 of the first locking element 10. Thus the relationship $V=(n+\frac{1}{2})\cdot a$, where n is a natural number, applies for the offset V of a particular second tooth 13 of the second locking element 12 compared to any second tooth 11 of the first locking element 10.

Figure 4:
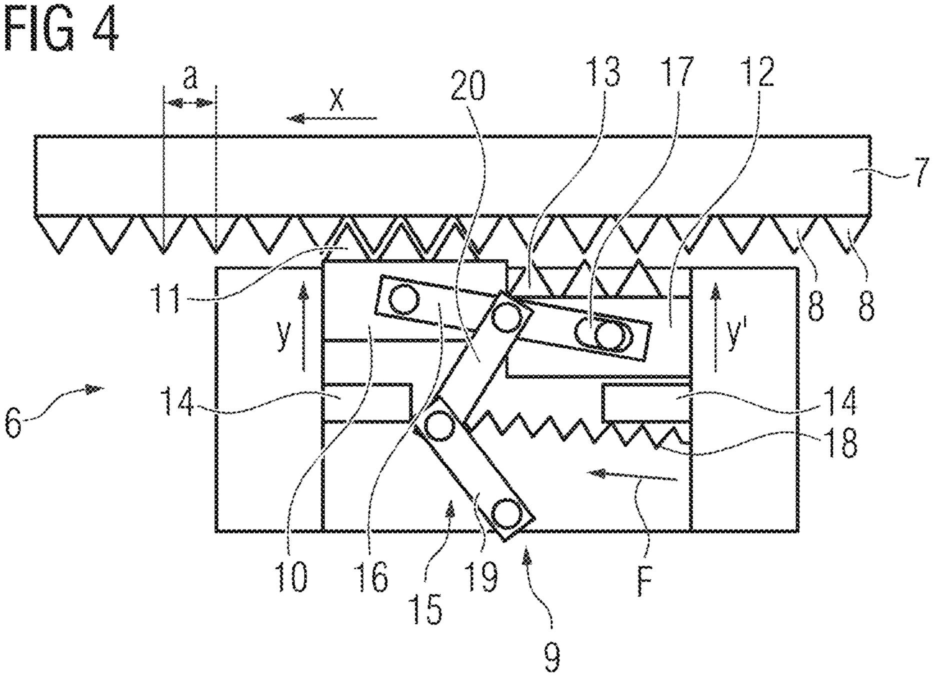
FIG. 4 the locking structure and the toothed element from FIG. 3, wherein a first locking element of the locking structure is in an actuation position, FIG. 5 the locking structure and the toothed element from FIG. 3, wherein a second locking element of the locking structure is in an actuation position, and FIG. 6 the locking structure and the toothed element from FIG. 3, wherein a first and a second locking element of the locking structure are each partially in an actuation position.
Figure 5:
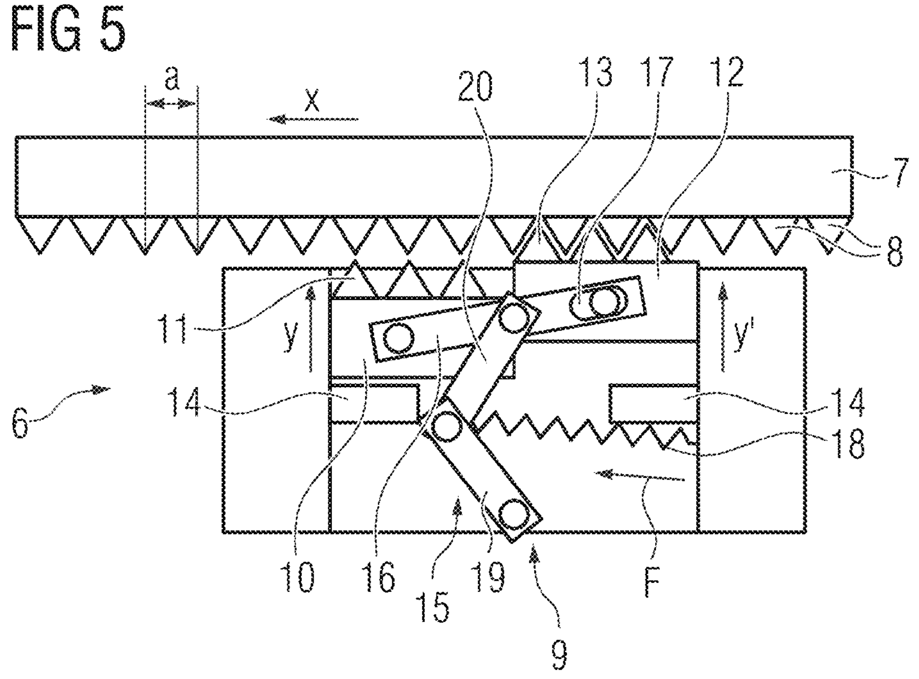
Figure 6:
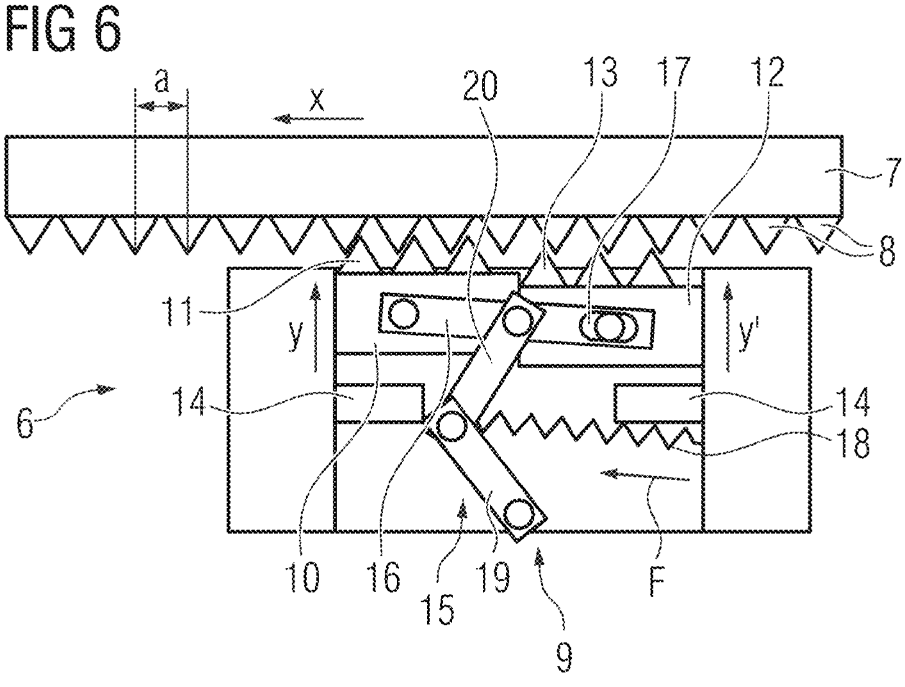

Because of the offset V, it is the case that if, because of the specific position of the first teeth 8 of the toothed element 7, the first locking element 10 can be transferred to its actuation position, the second locking element 12 cannot be transferred to its actuation position. This state is shown in FIG. 4. Because of the offset V, the reverse is also the case, namely that if the second locking element 12 can be transferred to its actuation position because of the specific position of the first teeth 8 of the toothed element 7, the first locking element 10 cannot be transferred to its actuation position. This state is shown in FIG. 5. However, because of the fact that in both cases one of the two locking elements 10, 12 can be transferred to its actuation position, a blocking of the travel movement of the additional body 2 relative to the base body 1 can nevertheless still be reliably achieved in both cases.

Even between these two extremes, in which one locking element 10 or 12 can be fully transferred to its actuation position and the other locking element 12 or 10 in each case cannot be transferred to its actuation position, a blocking of the travel movement of the additional body 2 relative to the base body 1 can be achieved because of the offset V of the second teeth 13 of the second locking element 12 compared to the teeth 11 of the first locking element 10 due to the interaction of both the locking elements 10, 12 with the toothed element 7. This is because in positions of the toothed element 7 between these two extremes, in accordance with FIG. 6 both locking elements 10, 12 each partially enter between the first teeth 8 of the toothed element 7. In this case the second teeth 11, 13 of both the locking elements 10, 12 in accordance with FIG. 6 rest on opposing flanks of the first teeth 8. For example, in the specific situation in FIG. 6 the first locking element 10 blocks a movement of the toothed element 7 and thus of the additional body 2 to the right, and the second locking element 12 blocks a movement of the toothed element 7 and thus of the additional body 2 to the left. The reverse situation is also possible.

FIGS. 3 to 6 show not only the basic principle of embodiments of the present invention, but also certain embodiments. These embodiments can be implemented independently of one another, provided they do not necessarily build on one another.

Thus the locking structure 6 for both the locking elements 10, 12 has a stop 14 in each case. In the release position of the respective locking element 12, 14, in accordance with FIG. 3 the respective locking element 10, 12, viewed in the respective direction of actuation y, y', rests on its respective stop 14.

Furthermore, the locking structure 6 has a uniform actuation element 15, by which the locking elements 10, 12 can be displaced between their release positions and their actuation positions. For example, the actuation element 15 can act on a connecting element 16, via which both the locking elements 10, 12 are connected to one another. The actuation element 15 can in particular act in a region of the connecting element 16 on the connecting element 16 which is situated between both the locking elements 10, 12, in particular approximately or exactly centrally between both the connecting elements 10, 12.

As explained above and as is in particular apparent from the illustrations in FIGS. 4 and 5, the second teeth 11, 13 of both the locking elements 10, 12 enter, depending on the position of the first teeth 8 of the toothed element 7 compared to the second teeth 11, 13, by a different distance between the first teeth 8. If there were a clearance-free connection of the connecting element 16 with both locking elements 10, 12, this could easily lead to jamming. To prevent such jamming, the connecting element 16 is connected to at least one of the locking elements 10, 12 via an elongated hole 17. The extent to which the elongated hole 17 is an elongated hole is clearly exaggerated in FIGS. 3 to 6 in order to better illustrate the facts.

For reasons of operational safety a spring facility 18 (also referred to as a spring device or spring) is preferably associated with the actuation element 15. The spring facility 18 exerts a spring force F on the actuation element 15. The spring force F is directed such that in the absence of a release force F' exerted on the actuation element 15 in the (common) direction of actuation y, y' the actuation element 15 applies to the locking elements 10, 12 a force to be directed to the actuation position. The spring facility is designed as a compression spring in FIGS. 3 to 6. However, it could also be designed as a tension spring.

In accordance with the illustration in FIGS. 3 to 6 the current preference is for the actuation element 15 to be designed as a toggle lever having a first and a second lever arm 19, 20. Consequently, when the locking elements 10, 12 move from their release positions (see FIG. 3) to their actuation positions (see FIGS. 4 to 6) it is in particular possible for the actuation element 15 to pass through an intermediate position, in which the first and the second lever arm form an angle of 180°. This always applies, i.e. regardless of the extent to which the additional body 2 has moved relative to the base body 1. It therefore applies both if, in accordance with the illustration in FIG. 4, the first locking element 10 can be moved fully into its actuation position, and if, in accordance with the illustration in FIG. 5, the second locking element 12 can be moved fully into its actuation position, as well as if, in accordance with the illustration in FIG. 6, the first and the second locking element 10, 12 can each only be partially moved into their actuation positions. The transfer of the locking elements 10, 12 from their (full or partial) actuation positions to their release positions can be effected by the exertion of the release force F'.

It has furthermore been explained above that both the locking elements 10, 12, viewed in the local direction of movement x, are arranged behind one another. However, this is not absolutely essential. Both the locking elements 10, 12 can equally also be arranged next to one another.

Embodiments of the present invention have many advantages. The moving masses can be kept small when moving the additional body 2 manually relative to the base body 1. The expense of a magnetically actuated disk brake or the like can be avoided. Nevertheless, it is possible to block the travel movement of the additional body 2 relative to the base body 1 in any position of the additional body 2.

The drawings are to be regarded as being schematic representations and elements illustrated in the drawings are not necessarily shown to scale. Rather, the various elements are represented such that their function and general purpose become apparent to a person skilled in the art. Any connection or coupling between functional blocks, devices, components, or other physical or functional units shown in the drawings or described herein may also be implemented by an indirect connection or coupling. A coupling between components may also be established over a wireless connection. Functional blocks may be implemented in hardware, firmware, software, or a combination thereof.

It will be understood that, although the terms first, second, etc. may be used herein to describe various elements, components, regions, layers, and/or sections, these elements, components, regions, layers, and/or sections, should not be limited by these terms. These terms are only used to distinguish one element from another. For example, a first element could be termed a second element, and, similarly, a second element could be termed a first element, without departing from the scope of embodiments. As used herein, the term "and/or," includes any and all combinations of one or more of the associated listed items. The phrase "at least one of" has the same meaning as "and/or".

Spatially relative terms, such as "beneath," "below," "lower," "under," "above," "upper," and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below," "beneath," or "under," other elements or features would then be oriented "above" the other elements or features. Thus, the example terms "below" and "under" may encompass both an orientation of above and below. The device may be otherwise oriented (rotated 90 degrees or at other orientations) and the spatially relative descriptors used herein interpreted accordingly. In addition, when an element is referred to as being "between" two elements, the element may be the only element between the two elements, or one or more other intervening elements may be present.

Spatial and functional relationships between elements (for example, between modules) are described using various terms, including "on," "connected," "engaged," "interfaced," and "coupled." Unless explicitly described as being "direct," when a relationship between first and second elements is described in the disclosure, that relationship encompasses a direct relationship where no other intervening elements are present between the first and second elements, and also an indirect relationship where one or more intervening elements are present (either spatially or functionally) between the first and second elements. In contrast, when an element is referred to as being "directly" connected, engaged, interfaced, or coupled to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of the embodiments. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items. Expressions such as "at least one of," when preceding a list of elements, modify the entire list of elements and do not modify the individual elements of the list. Also, the term "example" is intended to refer to an example or illustration.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Unless otherwise defined, all terms (including technical and scientific terms) used herein have the same meaning as commonly understood by one of ordinary skill in the art to which embodiments belong. It will be further understood that terms, e.g., those defined in commonly used dictionaries, should be interpreted as having a meaning that is consistent with their meaning in the context of the relevant art and will not be interpreted in an idealized or overly formal sense unless expressly so defined herein.

It is noted that some embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed above. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order. Although the flowcharts describe the operations as sequential processes, many of the operations may be performed in parallel, concurrently or simultaneously. In addition, the order of operations may be re-arranged. The processes may be terminated when their operations are completed, but may also have additional steps not included in the figure. The processes may correspond to methods, functions, procedures, subroutines, subprograms, etc.

Specific structural and functional details disclosed herein are merely representative for purposes of describing embodiments. The present invention may, however, be embodied in many alternate forms and should not be construed as limited to only the embodiments set forth herein.

What is claimed is:

1. An apparatus comprising:

a base body;

an additional body mounted on the base body via a guide so that the additional body is movable relative to the base body along a path determined by the guide;

a locking structure arranged on the base body; and a toothed element arranged on the additional body, wherein the locking structure and the toothed element are configured to interact to block a movement of the additional body relative to the base body, the toothed element has a plurality of first teeth, which successively pass through an effective area of the locking structure when the additional body moves relative to the base body, when the plurality of first teeth pass through the effective area of the locking structure, a local direction of movement of the toothed element which is valid for the effective area of the locking structure is defined, the plurality of first teeth, viewed in the local direction of movement, follow one another in a grid dimension, the locking structure has a first locking element and a second locking element, each of the first locking element and the second locking element includes a number of second teeth, each of the first locking element and the second locking element are configured to move in a direction of actuation running orthogonally to the local direction of movement of the toothed element between a respective release position and a respective actuation position, each of the first locking element and the second locking element is fixed in the local direction of movement of the toothed element, in the respective release position, the number of second teeth of a respective locking element do not enter between the plurality of first teeth and consequently do not block the movement of the additional body relative to the base body, in the respective actuation position, the number of second teeth of the respective locking element enter fully between the plurality of first teeth and consequently block the movement of the additional body relative to the base body, and viewed in the local direction of movement of the toothed element, the number of second teeth of the second locking element are offset by an odd-numbered multiple of half of the grid dimension compared to the number of second teeth of the first locking element.

2. The apparatus as claimed in claim 1, wherein each of the first locking element and the second locking element has multiple second teeth, and the number of second teeth of the respective locking element, viewed in the local direction of movement, follow one another in an integer multiple of the grid dimension.

3. The apparatus as claimed in claim 2, wherein the respective locking element, viewed in the respective release position in a respective direction of actuation, rests on a respective stop.

4. The apparatus as claimed in claim 2, wherein the direction of actuation of the second locking element corresponds to the direction of actuation of the first locking element, and the first locking element and the second locking element are configured to move between respective release positions and respective actuation positions via a uniform actuation element.

5. The apparatus as claimed in claim 2, wherein the additional body is a reclining table of a patient couch, and the base body is a support element of the patient couch that supports the reclining table.

6. The apparatus as claimed in claim 1, wherein the respective locking element, viewed in the respective release position in a respective direction of actuation, rests on a respective stop.

7. The apparatus as claimed in claim 6, wherein the direction of actuation of the second locking element corresponds to the direction of actuation of the first locking element, and the first locking element and the second locking element are configured to move between respective release positions and respective actuation positions via a uniform actuation element.

8. The apparatus as claimed in claim 1, wherein a direction of actuation of the second locking element corresponds to a direction of actuation of the first locking element, and the first locking element and the second locking element are configured to move between respective release positions and respective actuation positions via a uniform actuation element.

9. The apparatus as claimed in claim 8, wherein the uniform actuation element is configured to act on a connecting element connecting the first locking element and the second locking element to one another.

10. The apparatus as claimed in claim 9, wherein the uniform actuation element is configured to act on the connecting element in a region of the connecting element, which is situated between the first locking element and the second locking element.

11. The apparatus as claimed in claim 10, wherein the connecting element is connected to at least one of the first locking element or the second locking element via an elongated hole.

12. The apparatus as claimed in claim 10, wherein a spring device is associated with the uniform actuation element, and the spring device is configured to exert a spring force on the uniform actuation element, so that in absence of other forces in the direction of actuation of the first locking element and the second locking element, the uniform actuation element applies a force directed to the respective actuation position.

13. The apparatus as claimed in claim 9, wherein the connecting element is connected to at least one of the first locking element or the second locking element via an elongated hole.

14. The apparatus as claimed in claim 9, wherein a spring device is associated with the uniform actuation element, and the spring device is configured to exert a spring force on the uniform actuation element, so that in absence of other forces in the direction of actuation of the first locking element and the second locking element, the uniform actuation element applies a force directed to the respective actuation position.

15. The apparatus as claimed in claim 8, wherein a spring device is associated with the uniform actuation element, the spring device is configured to exert a spring force on the uniform actuation element, so that in absence of other forces in the direction of actuation of the first locking element and the second locking element, the uniform actuation element applies a force directed to the respective actuation position.

16. The apparatus as claimed in claim 8, wherein the uniform actuation element is a toggle lever having a first lever arm and a second lever arm.

17. The apparatus as claimed in claim 16, wherein when the first locking element and the second locking element move from respective release positions to respective actuation positions, the uniform actuation element always passes through an intermediate position in which the first lever arm and the second lever arm form an angle of 180°, regardless of an extent by which the additional body has moved relative to the base body.

18. The apparatus as claimed in claim 1, wherein the path determined by the guide is a linear path.

19. The apparatus as claimed in claim 1, wherein the additional body is a reclining table of a patient couch, and the base body is a support element of the patient couch that supports the reclining table.

20. The apparatus as claimed in claim 1, wherein the first locking element and the second locking element each have multiple second teeth, and the number of second teeth of the respective locking element, viewed in the local direction of movement, follow one another in the grid dimension.

* * * * *